(12) United States Patent
Waltl

(10) Patent No.: US 12,282,007 B2
(45) Date of Patent: Apr. 22, 2025

(54) ALPHA RADIATION DETECTOR HAVING AN OPTICAL SENSOR FOR MEASURING THE RADON CONCENTRATION IN THE AMBIENT AIR

(71) Applicant: RadonTec GmbH, Wittislingen (DE)

(72) Inventor: Rudolf Waltl, Wittislingen (DE)

(73) Assignee: LIVAIR GMBH, Munich (DE)

( * ) Notice: Subject to any disclaimer, the term of this patent is extended or adjusted under 35 U.S.C. 154(b) by 292 days.

(21) Appl. No.: 17/778,680

(22) PCT Filed: Nov. 20, 2020

(86) PCT No.: PCT/EP2020/082984
§ 371 (c)(1),
(2) Date: May 20, 2022

(87) PCT Pub. No.: WO2021/099619
PCT Pub. Date: May 27, 2021

(65) Prior Publication Data
US 2022/0412934 A1 Dec. 29, 2022

(30) Foreign Application Priority Data
Nov. 21, 2019 (EP) .................................... 19210601

(51) Int. Cl.
*G01N 33/00* (2006.01)
(52) U.S. Cl.
CPC ............................... *G01N 33/0055* (2013.01)
(58) Field of Classification Search
CPC ................................................. G01N 33/0055
See application file for complete search history.

(56) References Cited

U.S. PATENT DOCUMENTS 4,186,303 A * 1/1980 Smith ...................... G01V 5/02
250/DIG. 2
4,476,388 A 10/1984 Yakubovich et al.
(Continued)

FOREIGN PATENT DOCUMENTS

CN 202362462 U * 8/2012
CN 206096475 U 4/2017
(Continued)

OTHER PUBLICATIONS

International Search Report for application No. PCT/EP2020/082984 mailed Feb. 22, 2021.
(Continued)

*Primary Examiner* — Dani Fox
*Assistant Examiner* — Fani Polyzos Boosalis
(74) *Attorney, Agent, or Firm* — Carter, DeLuca & Farrell LLP

(57) ABSTRACT

The invention relates to an alpha radiation detector (1) for measuring the radon concentration in the ambient air, comprising a housing (10) having a base (5) on which a hood (2) is arranged, which hood has a chamber (9) which is located therein, wherein the opaque housing (10) is designed in such a way that ambient air can penetrate into the chamber (9) from the outside, the alpha radiation detector further comprising an optical sensor (4). According to the invention, the hood (2) has an inner wall which is provided at least in part with a scintillation material (3) which generates light pulses (8) upon impingement of alpha particles (7), which light pulses are sensed by the optical sensor (4).

15 Claims, 4 Drawing Sheets

(56) References Cited

U.S. PATENT DOCUMENTS

| | | | |
|---|---|---|---|
| 4,704,537 | A | 11/1987 | Urban et al. |
| 4,871,914 | A | 10/1989 | Simon et al. |
| 4,894,535 | A | 1/1990 | Madnick et al. |
| 5,489,780 | A | 2/1996 | Diamondis |

FOREIGN PATENT DOCUMENTS

| | | | |
|---|---|---|---|
| DE | 231137 | C | 12/1985 |
| EP | 0470054 | A2 | 2/1992 |
| EP | 0412194 | B1 | 6/1993 |
| EP | 3252505 | B1 | 12/2018 |
| KR | 20170025395 | A | 3/2017 |
| KR | 101771476 | B1 | 8/2017 |
| KR | 20190000639 | A | 1/2019 |

OTHER PUBLICATIONS

Extended EP Search Report for application No. 19210601.1 dated May 29, 2020.

Yamamoto Set al: "Development of a continuous radon concentration monitoring system in underground soil", Nuclear Science Symposium Conference Record, 2000 IEEE Lyon, France Oct. 15-20, 2000, IEEE, US, Bd. 1, Oct. 15, 2000 (Oct. 15, 2000), pp. 6/313-6/316.

Mcdonald E Wrenn et al: "Design of a Continuous Digital-Output Environmental Radon Monitor", IEEE Transactions on Nuclear Science,, Bd. NS-22, Nr. 1, Feb. 1, 1975 (Feb. 1, 1975), pp. 645-648.

\* cited by examiner

ALPHA RADIATION DETECTOR HAVING AN OPTICAL SENSOR FOR MEASURING THE RADON CONCENTRATION IN THE AMBIENT AIR

The invention relates to an alpha radiation detector having an optical sensor for measuring the radon concentration in the ambient air.

BACKGROUND OF THE INVENTION

Radon is a radioactive noble gas which is created as an intermediate product during the radioactive decay of radium, actinium or thorium. It occurs naturally in certain rock layers, from where it can pass to the earth's surface. At the earth's surface, it collects preferably in the basements of buildings, where it sometimes reaches high concentrations. All known isotopes of radon are radioactive and emit alpha particles (or beta particles) as they decay. Since radon and its derived products (polonium, lead and bismuth) is breathed in by humans together with the ambient air, it is potentially harmful to health.

There are various approaches for measuring the radon concentration in the ambient air. One of these uses the property of scintillators, that is to say materials that emit a light pulse upon impingement of an alpha particle. The light pulses thus generated are then sensed by an optical sensor. The number and also the strength/intensity of the light pulses per time unit is a measure here for the radon concentration in the ambient air. The radon detectors having an optical sensor known from the prior art are all of a relatively complex design, costly, use a lot of energy, and are very large, or are not sufficiently sensitive or are slow. Various designs of alpha radiation detectors are known from CN 202 362 462 U, KR 2017 0025395 A or U.S. Pat. No. 5,489,780 A and also from YAMAMOTO S. ET AL: "Development of a continuous radon concentration monitoring system in underground soil", NUCLEAR SCIENCE SYMPOSIUM CONFERENCE RECORD, 2000 IEEE LYON, FRANCE 15-20 Oct. 2000, PISCATAWAY, NJ, USA, IEEE, US, vol. 1, 15 Oct. 2000 (2000 Oct. 15), pages 6/313-6/316, XP010556576, DOI: 10.1109/NSSMIC.2000.949228, ISBN: 978-0-7803-6503-2 and from MCDONALD E. WRENN ET AL: "DESIGN OF A CONTINUOUS DIGITAL-OUTPUT ENVIRONMENTAL RADON MONITOR", IEEE TRANSACTIONS ON NUCLEAR SCIENCE, vol. NS-22, no. 1, 1 Feb. 1975 (1975 Feb. 1), pages 645-648, XP001446806.

OBJECT OF THE INVENTION

The object of the present invention is therefore to create an alpha radiation detector having an optical sensor which is constructed much more simply, so as to be very small, very energy-saving, very sensitive, quick, and which can be produced more economically.

This problem is solved in accordance with the invention by the features described in claim 1. Further embodiments of the invention are the subject of dependent claims.

In accordance with the invention, an alpha radiation detector having an optical sensor for measuring the radon concentration in the ambient air is proposed, comprising a base on which there is arranged a hood having a measuring chamber which is located therein. At least a part of the inner wall of the hood is provided with a scintillation material which generates light pulses upon impingement of alpha particles, which light pulses are then sensed by the optical sensor. The electrical signals of the sensor are evaluated by means of an electrical circuit which on that basis determines a radon concentration. Such an alpha radiation detector is of very simple construction and can be made very small, in an energy-saving and economical manner.

In accordance with a first embodiment of the invention, the hood comprises a first portion, which is impermeable to light and on its inner wall is provided with a scintillation material which, upon impingement of alpha particles, generates light pulses which are sensed by the optical sensor, and a second preferably annular or peripheral portion which is produced from a material that is impermeable to light but is gas-permeable for radon.

The hood can be made in one part or in multiple parts, selectively. A one-part hood can have, for example, a first portion made of ceramic material impermeable to light and a second portion made of ceramic material that is impermeable to light, but gas-permeable for radon. The second portion can be produced for example by etching the ceramic material in a certain region.

A multi-part hood can comprise at least two separate elements which, when assembled together, are preferably arranged one above the other and form the stated hood. The two elements preferably correspond to the above-mentioned first and second portion. They can be, for example, bonded to one another, mechanically fastened to one another, or connected to one another in some other way.

The material thickness, the structure and the tightness of the gas-permeable material are preferably selected such that no light, but sufficient ambient air or radon gas can pass into the chamber. Furthermore, the material is preferably selected such that any already decaying radon, that is to say polonium, lead or bismuth, cannot penetrate into the chamber from outside. Since these subsequent decays of radon are ionized, they are not bound by the material and therefore cannot penetrate into the chamber. Dust or other aerosols cannot penetrate into the chamber, thus protecting the sensor against soiling.

The alpha radiation detector according to the invention is designed to measure fundamentally the concentration of the radon exiting from the ground or subsurface. Other gases present in the ambient air, such as thoron, which escapes above all from construction materials (loam walls, loam tiles, slate, granite, etc.), where possible, should not influence the measurement result or should only hardly influence it. In order to keep low the influence of thoron on the radon measurement, the gas-permeable portion or the gas-permeable material of the sensor according to the invention is preferably designed in such a way that thoron decays to an extent of more than 90%, preferably to an extent of about 99% as it passes through the portion or the air-permeable material, or rather less than 10% or less than 1% of the thoron present in the ambient air passes into the chamber. The permeability for thoron can be set as desired, for example, by the thickness of the material, its structure or porosity, and/or its density. A suitable material is, for example, Dinopur®, with an outer diameter of 50 mm and a wall thickness of 5 mm or an open-pore polyurethane foam.

The first portion of the hood, provided with scintillation material, can be produced for example from a metal, such as aluminum, for a ceramic material or from plastic. The second, annular portion made of gas-permeable material can be produced, for example, from felt, silicone, cloth, plastic, foam, a ceramic material or a membrane, or from another material having the stated properties.

The scintillation material is preferably applied only to the inner wall of the first portion of the hood; the inner wall of the second, annular portion of the hood is preferably not provided with scintillation material.

The radon detector of the first embodiment preferably comprises an assembly device having a first and a second mounting element which are connectable to one another and are designed to press the hood against the base when the two assembly elements are joined together. The first mounting element can engage, for example, the first portion of the hood and can exert a force on the hood, acting in the direction of the base; the second mounting element can be arranged on the other side of the base (in particular the underside) and can press the base against the hood.

The mounting elements can have, for example, corresponding elements of a detent connection. Alternatively, a screw connection or another known connection mechanism could also be provided to connect the two mounting elements.

The mounting elements are produced from a material that is impermeable to light, but is preferably permeable for radon gas by diffusion. A possible material is, for example, Cellidor® from the company ALBIS. The material may also be electrically conductive.

According to a special embodiment of the invention, the first portion of the hood comprises a protrusion that protrudes beyond the contour of the portion, such as an outwardly protruding lip or a flanged edge which is engaged by the first mounting element.

The first mounting element can have, for example, an opening which is dimensioned such that only a part of the hood fits through, but another part does not. The second mounting element can be plate-shaped, for example. Both mounting elements are preferably equipped with corresponding elements of a detent connection.

A second embodiment of an alpha radiation detector likewise comprises a base on which there is arranged a hood in which there is located a measuring chamber. The optical sensor is preferably arranged on the base within the chamber. The hood is provided at least on a portion of its inner wall with a scintillation material which, upon impingement of alpha particles, generates light pulses which are sensed by the optical sensor. In contrast to the first embodiment, the base here is designed in such a way that ambient air can penetrate into the chamber from outside through the base. The base, for this purpose, has at least one aperture, which is closed by the material that is impermeable to light, but permeable to gas, so that ambient air can penetrate into the chamber from outside. The hood is produced from a material that is impermeable to light, such as plastic or metal, and can be a one-piece component, for example. It can likewise be permeable to radon gas, similarly to the base.

In a radon detector as per the second embodiment, a first and a second mounting element are preferably provided, which are connectable to one another and are designed to press the base and the gas-permeable material arranged under the base together when the mounting elements are joined together.

In the second embodiment the hood preferably functions as the first mounting element. The second mounting element is preferably arranged on the other side (in particular the underside) of the base; for example, it can be plate-shaped. Both assembly elements can in turn have corresponding elements of a detent connection. Alternatively, a screw connection or another known connection mechanism could also be provided for connecting the two assembly elements.

The second mounting element preferably has at least one opening, through which ambient air can pass into the alpha radiation detector from outside.

The gas-permeable material can be mounted within the aperture provided, selectively, in the base, on the inner side of the base and/or on the outer side of the base. In accordance with a preferred embodiment of the invention, the gas-permeable material is formed as a plate which is arranged on the underside (or outer side) of the base.

The above-mentioned scintillation material can be, for example, zinc sulfide, bismuth germanate, lead tungstate, lutetium oxyorthosilicate, sodium iodide, zinc sulfide or cesium iodide.

The hood arranged on the base can have a dome shape, for example. It can be designed, for example, as part of a sphere and can be formed for example in a hemispherical or pyramidal shape. However, it can also be cylindrical or angular, for example square.

The optical sensor is preferably a photomultiplier, in particular a SiPM. The optical sensor is preferably arranged within the measuring chamber, in particular on the base, and preferably lies on an axis of symmetry of the hood.

The base can be formed for example in a plate shape. In accordance with a preferred embodiment of the invention, the base consists of a printed circuit board material. This has the advantage that the evaluation electronics can be arranged similarly on or below the base.

BRIEF DESCRIPTION OF THE DRAWINGS

The invention will be explained by way of example in greater detail hereinafter with reference to the appended drawing, in which:

FIGS. 1 and 2 show a first embodiment of an alpha radiation or radon detector 1 with a base 5, on which there is arranged a hemispherical hood 2. A chamber 9 is located within the hood 2 and represents a measuring cell in which the radon concentration is measured. An optical sensor 4, such as a SiPM, is arranged on the base 5 and detected the light pulses generated during alpha decay.

Figure 1:
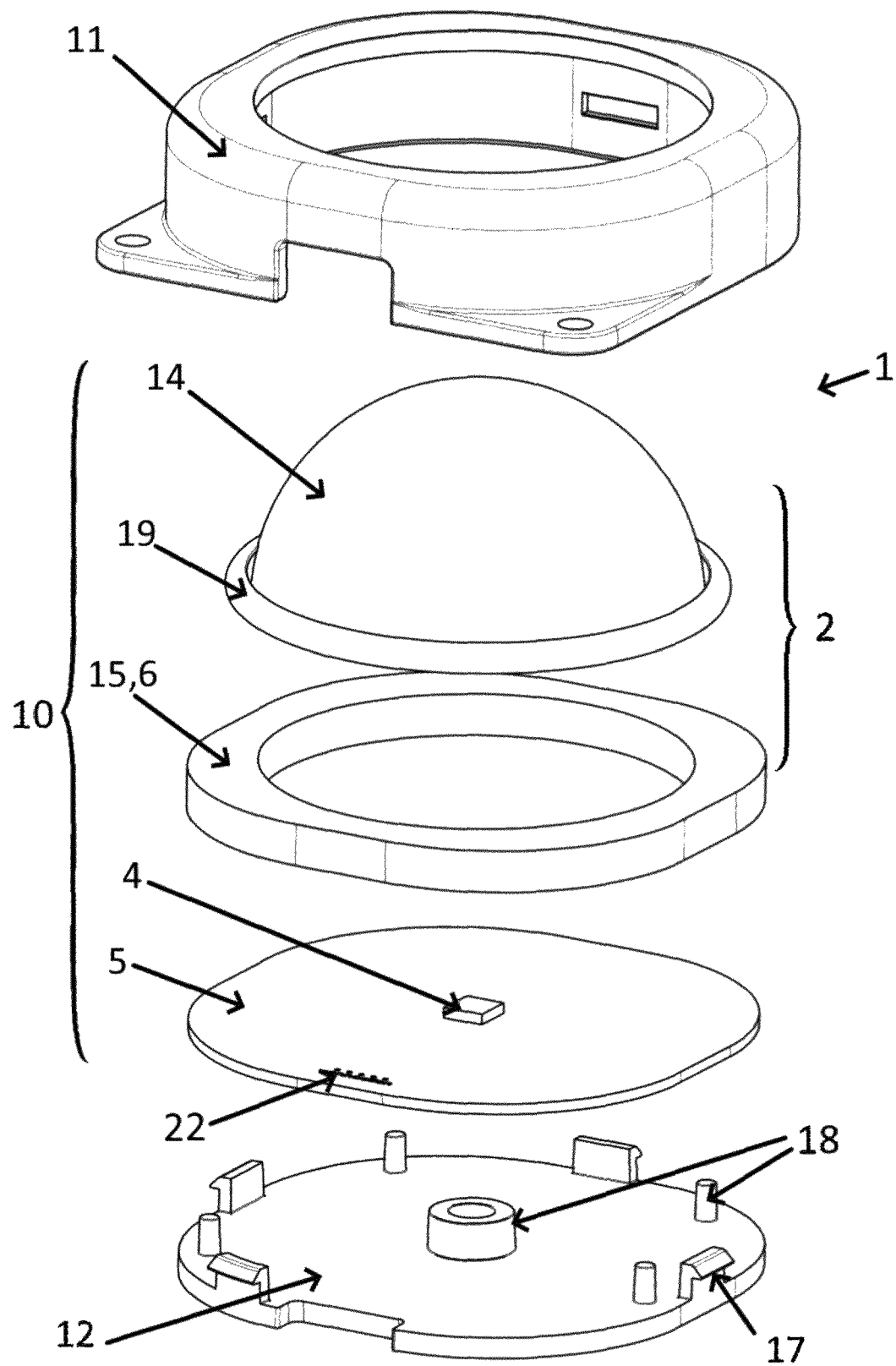
FIG. 1 shows an exploded view of an alpha radiation detector according to a first embodiment.
Figure 2:
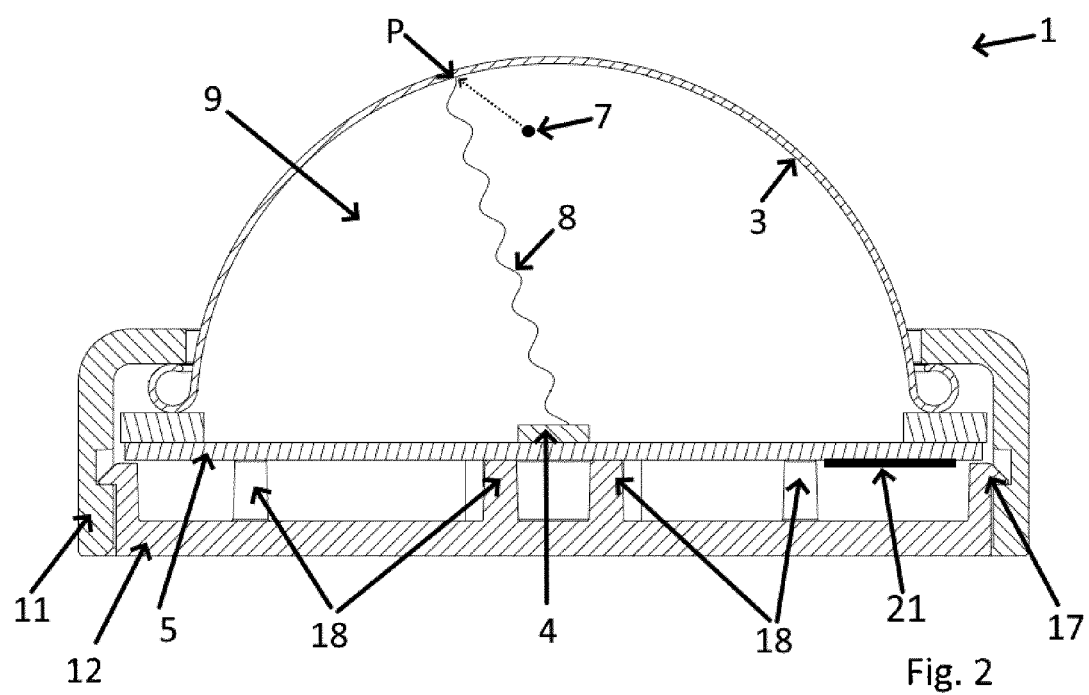
FIG. 2 shows a side view of the alpha radiation detector of FIG. 1.

The base 5 together with the hood 2 located thereon form a housing 10 which completely surrounds the chamber 9, so that no light can penetrate into the chamber 9 from outside. In the embodiment shown in FIGS. 1 and 2, the hood 2 is formed in a number of parts and comprises a first portion 14, which is impermeable to light and is provided on its inner wall with a scintillation material 3, which, upon impingement of alpha particles, generates light pulses which are sensed by the optical sensor 4. The hood 2 further comprises a second, annular portion 15, which is produced from a material 6 that is impermeable to light, but permeable to air or gas, such as a (open-pore) foam. The two portions 14, 15, when assembled together, lie one above the other and are pressed together with the base 5 by first and second mounting elements 11, 12.

The first portion 14 of the hood 2 can be produced for example from metal, ceramic or a plastic.

The first portion 14 of the hood 2, in the embodiment shown here, has an edge 19 which protrudes outwardly beyond the contour of the portion 14 and which is engaged by the first mounting element 11. The second mounting element 12 is arranged on the other side of the base 5 and forms a bottom of the arrangement. Both mounting elements 11, 12 comprise corresponding elements of a detent connection 17, which make it possible to assembly the radon detector 1 quickly and easily and, as the mounting elements 11, 12 are joined together, to press the first portion 14 of the hood 2 simultaneously against the annular or peripheral portion 15 and the base 5. A plurality of protrusions 18 are also provided on the second mounting element 12 and press against the base 5 from below.

The gas-permeable material 6 can comprise, for example, felt, silicone, foam, a plastic, or a membrane. The wall thickness and the structure/the tightness of the material 6 is selected in such a way that it is impermeable to light present at the site of use, however, a sufficient exchange of ambient air into and out from the chamber 9 may occur.

As mentioned at the outset, radon decays under radiation of alpha particles into further decay products. The decay products, such as polonium, also then decay again with alpha radiation. An alpha particle 7 is shown by way of example in FIG. 2. The alpha particle 7 moves in the direction of the dashed arrow and impinges at a point P against the scintillation material 3 located on the inner wall of the hood 2. The scintillation material in turn emits an optical light pulse 8, which is then detected by the optical sensor 4. The scintillation material 3 is preferably a layer of zinc sulfide (ZnS:Cu, ZnS:AG). Alternatively, other materials known from the prior art could also be used.

The base 5 preferably comprises a printed circuit board, on or below which an evaluation electronics 21 can also be arranged. In the shown exemplary embodiment, the evaluation electronics 21 is located beneath the printed circuit board. As can be seen, the evaluation electronics 21 is not located directly beneath the sensor 4, but is arranged at the greatest possible distance from the sensor 4 in order to keep the influence of electromagnetic radiation on the sensor 4 low and to avoid interference.

The optical sensor 4 is preferably a silicon photomultiplier. In the shown exemplary embodiment the optical sensor 4 sits on the bottom of the chamber 9 on the base 5. The photomultiplier is preferably arranged on an axis of symmetry of the hood on the base 5.

An optical unit for bundling the light pulses 8 may be provided, but does not have to be.

Figure 3:
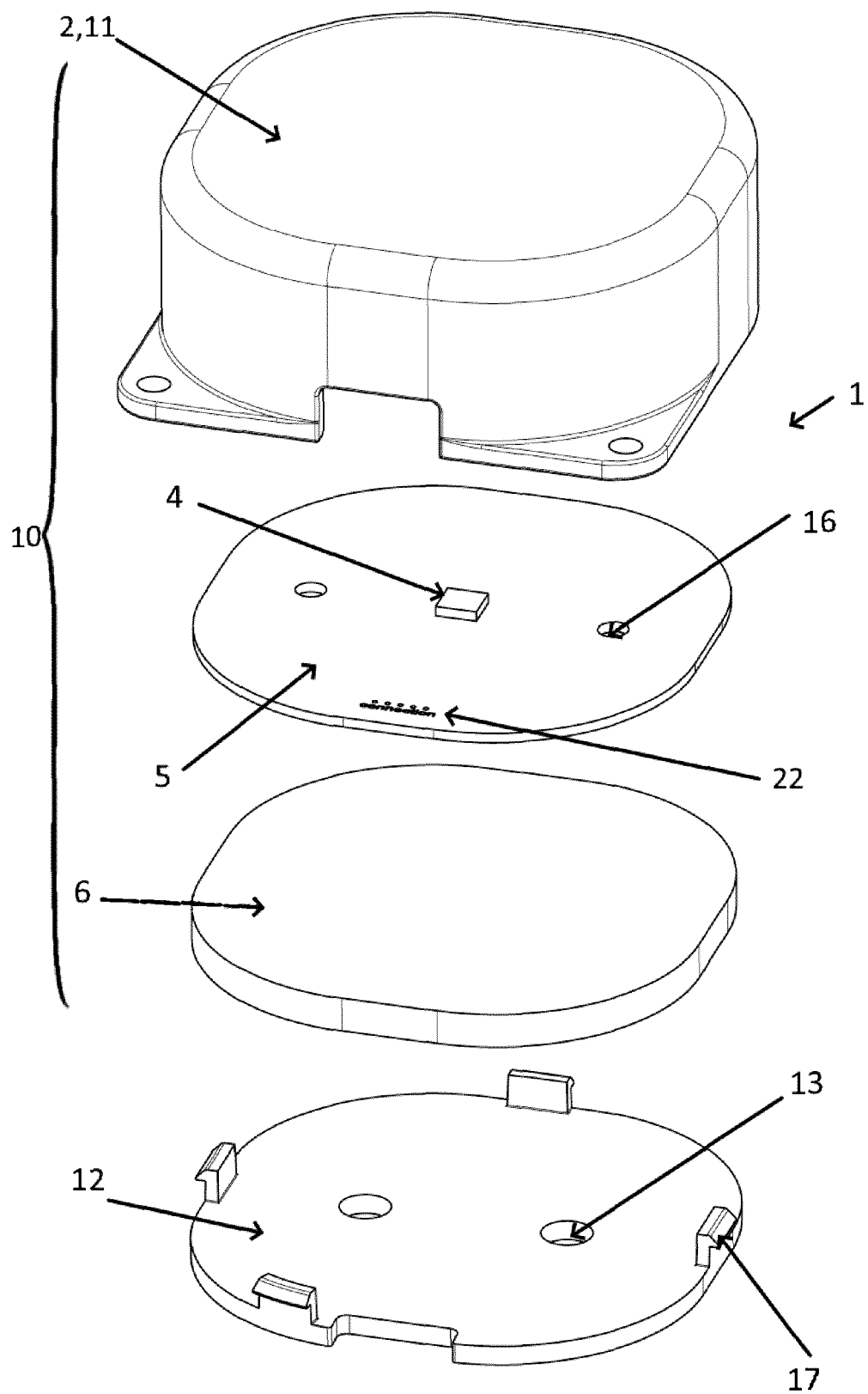
FIG. 3 shows an exploded view of an alpha radiation detector according to a second embodiment.
Figure 4:
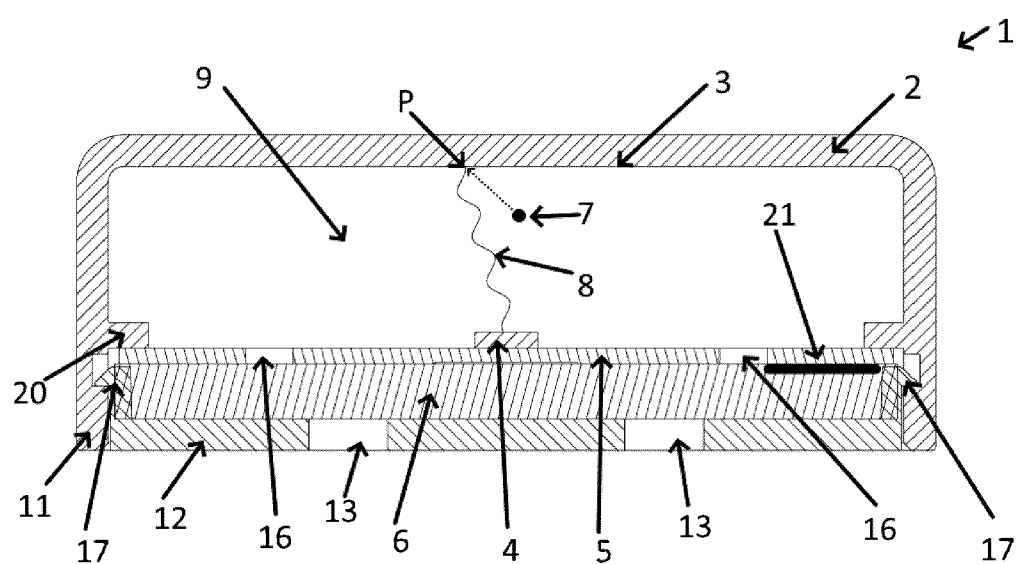
FIG. 4 shows a side view of the alpha radiation detector from FIG. 3.

FIGS. 3 and 4 show a second embodiment of an alpha radiation or radon detector 1 having a base 5 on which a hood 2 is arranged. A chamber 9 is in turn located within the hood 2 and represents a measuring cell, in which the radon concentration is measured.

The hood 2 is provided on its inner wall with a scintillation material 3, which, upon impingement of alpha particles, generates light pulses which are sensed by an optical sensor 4. In contrast to the first embodiment, the base 5 is formed in such a way that ambient air can pass from outside through the base 5 and into the chamber 9. The base 5 for this purpose has at least one aperture 16, which is closed by the material 6 that is impermeable to light but permeable to gas.

The gas-permeable material 6 is plate-shaped here and is located beneath the base 5. The hood 2 is located on the upper side of the base 5 and preferably consists of a material that is impermeable to light, such as plastic or metal.

In the radon detector 1 as per the second embodiment, the hood 2 and a second mounting element 12 are designed to press the gas-permeable material 6 against the base 5 when the hood 2 is connected to the second mounting element 12. The second mounting element 12 is located on the underside of the base 5 and forms a bottom of the arrangement. The above-mentioned gas-permeable material 16 is located between the second mounting element 12 and the base 5. Both parts 2, 12 are equipped with corresponding elements of a detent connection 17.

The hood 2 comprises an inwardly protruding stop 20, which engages a surface of the base 5. When the hood 2 and the second mounting element 12 are joined together, the base 5 and the gas-permeable material 6 are clamped between the two parts 2, 12.

The second mounting element 12 comprises at least one further opening 13, through which ambient air can penetrate into the radon detector 1 from outside. The ambient air then passes through the gas-permeable material 6 and the aperture 16 into the chamber 9.

The signals generated by the sensor 4 are processed by the evaluation electronics 21 and provides corresponding electrical analogue or digital signals, which can be tapped via an interface 22. The radon detector 1 can also comprise one or more interfaces 22 for peripheral devices, such as display units or computers.

The invention claimed is:

1. An alpha radiation detector for measuring radon concentration in ambient air, the alpha radiation detector comprising:
   a housing having a base on which there is arranged a hood having a chamber which is located therein, the housing being configured in such a way that ambient air can penetrate into the chamber from outside, and
   an optical sensor;
   the hood having a first portion having an inner wall, which is provided with a scintillation material which generates light pulses upon impingement of alpha particles, which light pulses are sensed by the optical sensor, wherein the hood has a second portion formed as a ring which is made of a material that is impermeable to light but permeable to gas, so that radon gas can penetrate into the chamber from outside through a wall of the ring in a direction that is transverse to a circumferential direction of the ring, wherein the first portion and the second portion are arranged on top of each other.

2. The alpha radiation detector according to claim 1, wherein the hood is made as a single piece and the first portion that is impermeable to light and the second portion is impermeable to light, but permeable to gas.

3. The alpha radiation detector according to claim 1, wherein the gas-permeable material comprises felt, silicone, cloth, plastic, foam, a ceramic material, or a membrane.

4. The alpha radiation detector according to claim 1, wherein the scintillation material comprises doped zinc sulfide, bismuth germanate, lead tungstate, lutetium oxyorthosilicate, sodium iodide, zinc sulfide, or cesium iodide.

5. The alpha radiation detector according to claim 1, wherein the optical sensor is arranged within the chamber, on the base.

6. The alpha radiation detector according to claim 1, wherein the optical sensor is a silicon photomultiplier.

7. The alpha radiation detector according to claim 1, wherein the optical sensor is arranged in the chamber.

8. The alpha radiation detector according to claim 1, wherein the base is plate-shaped.

9. The alpha radiation detector according to claim 1, wherein the base is made of a printed circuit board material and is equipped with an evaluation electronics.

10. The alpha radiation detector according to claim 1, wherein a first and a second mounting element are provided, which are configured such that the first and second mounting elements press the hood against the base when the first and second mounting elements are joined together.

11. The alpha radiation detector according to claim 10, wherein the first mounting element has an opening which is dimensioned such that only a part of the hood fits through, the second mounting element is plate-shaped, and both mounting elements comprise corresponding elements of a detent connection, by means of which they are connected.

12. An alpha radiation detector for measuring radon concentration in ambient air, the alpha radiation detector comprising:
   a housing having a base on which there is arranged a hood having a chamber which is located therein, the housing being configured in such a way that ambient air can penetrate into the chamber from outside, and
   an optical sensor; wherein:
      the base is made of a printed circuit board material and is equipped with
   an evaluation electronics;
      the optical sensor is arranged within the chamber, on the base;
      the optical sensor is a silicon photomultiplier; and
      the base has at least one aperture, which is closed by a material that is impermeable to light but permeable to gas, so that radon gas can pass into the chamber from outside, through the aperture.

13. The alpha radiation detector according to claim 12, wherein the gas-permeable material is arranged on an underside of the base, and a first mounting element and a second mounting element are provided, which are configured such that the gas-permeable material is pressed against the underside of the base when the first and second mounting elements are joined together.

14. The alpha radiation detector according to claim 13, wherein the hood is formed as the first mounting element, the second mounting element is plate-shaped, and both mounting elements comprise corresponding elements of a detent connection, by means of which they are connected to one another.

15. An alpha radiation detector for measuring radon concentration in ambient air, the alpha radiation detector comprising:
   a housing having a base on which there is arranged a hood having a chamber which is located therein, the housing being configured in such a way that ambient air can penetrate into the chamber from outside, and
   an optical sensor,
   wherein the hood includes:
   an inner wall having a scintillation material which generates light pulses upon impingement of alpha particles, the light pulses being sensed by the optical sensor;
   an annular portion which is made of a material that is impermeable to light but permeable to gas, so that radon gas can penetrate into the chamber from outside; and
   a first portion which is impermeable to light and a second portion which is impermeable to light, but permeable to gas.

* * * * *